US010905705B2

(12) United States Patent
Kumagai et al.

(10) Patent No.: US 10,905,705 B2
(45) Date of Patent: *Feb. 2, 2021

(54) AGENT FOR PREVENTING OR IMPROVING DECLINE IN BRAIN FUNCTION (71) Applicant: KYOWA HAKKO BIO CO., LTD., Tokyo (JP)

(72) Inventors: Kota Kumagai, Tsukuba (JP); Masahiko Morita, Tsukuba (JP); Takahiro Hara, Tsukuba (JP); Kohji Fukunaga, Sendai (JP)

(73) Assignee: KYOWA HAKKO BIO CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/435,984

(22) PCT Filed: Oct. 30, 2013

(86) PCT No.: PCT/JP2013/080053
§ 371 (c)(1),
(2) Date: Apr. 15, 2015

(87) PCT Pub. No.: WO2014/069667
PCT Pub. Date: May 8, 2014

(65) Prior Publication Data
US 2015/0306125 A1 Oct. 29, 2015

(30) Foreign Application Priority Data

Oct. 30, 2012 (JP) .................. 2012-238542

(51) Int. Cl.
*A61K 31/7068* (2006.01)
*A61K 31/198* (2006.01)

(52) U.S. Cl.
CPC ........ *A61K 31/7068* (2013.01); *A61K 31/198* (2013.01)

(58) Field of Classification Search
None
See application file for complete search history.

(56) References Cited

U.S. PATENT DOCUMENTS

2001/0056068 A1  12/2001  Chwalisz et al.
2006/0046982 A1   3/2006  Waugh

FOREIGN PATENT DOCUMENTS

WO   WO 2009/096505 A1   8/2009

OTHER PUBLICATIONS

McGlade, E. et al., Food and Nutrition Sciences, "Improved Attentional Performance Following Citicoline Administration in Healthy Adult Women", Jun. 2012, vol. 3, No. 6, pp. 769-773.*
McGlade, E. et al., Food and Nutrition Sciences, "Improved Attentional Performance Following Citicoline Administration in Healthy Adult Women", Jun. 2012, vol. 3, pp. 769-773.*
Ochiai et al., machine translation of WO2009/096505, obtained Sep. 15, 2016 using Google translate.*
WordNet Search 3.0, "prevent"; available at http://wordnet.princeton.edu; last viewed Nov. 14, 2007.*
Reagan-Shaw, S. et al., FASEB Journal, "Dose translation from animal to human studies revisted", 2007, vol. 22, pp. 659-661 (Year: 2007).*
Nair, A. B. et al., Journal of Basic and Clinical Pharmacy, "A simple practice guide for dose conversion between animals and human", 2016, vol. 7, pp. 27-31 (Year: 2016).*
Hattori, Y. et al., PLOS ONE, "A novel mouse model of ischemic carotid artery disease", 2014, vol. 9, No. 6, 7 pages (Year: 2014).*
Bruhwyler et al., *Progress in Neuro-Psychopharmacology & Biological Psychiatry*, 22(1): 115-128 (1998).
Zhao et al., *Journal of Southern Medical University*, 26(2): 174-176 (2006).
European Patent Office, Supplementary European Search Report in European Patent Application No. 13 85 0415 (Feb. 15, 2016).
Alvarez et al., "Double-blind Placebo-Controlled Study with Citicoline in APOE Genotype Alzheimer's Disease Patients. Effects on Cognitive Performance, Brain Bioelectrical Activity and Cerebral Perfusion," *Methods and Findings in Experimental and Clinical Pharmacology*, 21-9: 633-644 (1999).
Curis et al., "Almost All About Citrulline in Mammals," *Amino Acids*, 29: 177-205 (2005).
Davalos et al., "Oral Citicoline in Acute Ischemic Stroke: An Individual Patient Data Pooling Analysis of Clinical Trials," *Stroke*, 33: 2850-2857 (2002).
Hayashi et al., "L-citrulline and L-arginine supplementation retards the progression of high-cholesterol-diet-induced atherosclerosis in rabbits," *PNAS*, 102(38): 13681-13686 (Sep. 20, 2005).
Jong et al., "Cerebral Hypoperfusion Yields Capillary Damage in the Hippocampal CA1 Area that Correlates with Spatial Memory Impairment," *Neuroscience*, 91(1): 203-210 (1999).
Khavandgar et al., "The effect of L•NAME and L-arginine on impairment of memory formation and state-dependent learning induced by morphine in mice," *Psychopharmacology*, 167: 291-296 (2003).
Okamura, "Effect of Mental Fatigue Induced by Repeated Continuous Calculation Tasks on Event-related Brain Potential,", *Journal of Occupational Health*, 49: 203-208 (2007).
Rao et al., "CDP-Choline: Neuroprotection in Transient Forebrain Ischemia of Gerbils," *Journal of Neuroscience Research*, 58: 697-705 (1999).
Japan Patent Office, International Search Report in International Patent Application No. PCT/JP2013/080053 (Feb. 10, 2014).

(Continued)

*Primary Examiner* — Bahar Craigo
(74) *Attorney, Agent, or Firm* — Leydig, Voit & Mayer, Ltd.

(57) ABSTRACT

An objection of the present invention is to provide an agent for preventing or improving decline in brain function such as decreased perception ability, decreased memory learning ability, decreased thinking ability, decreased concentration, decreased attention, decreased judgment ability, depression, and decreased exercise performance caused thereby. According to the present invention, an agent for protecting brain neuronal cells, comprising citrulline or a salt thereof and citicoline or a salt thereof as active ingredients as well as an agent for preventing or improving decline in brain function, comprising citrulline or a salt thereof and citicoline or a salt thereof as active ingredients is provided.

14 Claims, 4 Drawing Sheets (56) References Cited

OTHER PUBLICATIONS

U.S. Department of Health and Human Services, Food and Drug Administration (FDA), "Guidance for Industry: Estimating the Maximum Safe Starting Dose in Initial Clinical Trials for Therapeutics in Adult Healthy Volunteers" (Jul. 2005).
Alvarez et al., "Citicoline Improves Memory Performance in Elderly Subjects," *Methods Find. Exp. Clin. Pharmacol.*, 19(3): 201-210 (1997).
Fioravanti et al., "Cytidinediphosphocholine (CDP-choline) for cognitive and behavioural disturbances associated with chronic cerebral disorders in the elderly (Review)," *The Cochrane Collaboration*, 1-35 (2009).
Morita et al., "Effects of Oral L-Citrulline Supplementation on Lipoprotein Oxidation and Endothelial Dysfunction in Humans with Vasospastic Angina," *Immunol. Endocr. Metab. Agents Med. Chem.*, 13(3): 214-220 (2013).
Takasaki et al., "Citidine-5-diphosphocholine Ameliorates the Impairment of Spatial Memory Induced by Scopolamine," *Journal of Health Science*, 57(5): 432-435 (2011).
Takasaki et al., "Neuroprotective Effects of Citidine-5-diphosphocholine on Impaired Spatial Memory in a Rat Model of Cerebrovascular Dementia," *J. Pharmacol. Sci.*, 116(2): 232-237 (2011).
Fresina et al., "Effect of oral CDP-choline on visual function in young amblyopic patients," *Graefes Arch. Clin. Exp. Ophthalmol.*, 246(1): 143-150 (2008).
Spiers et al., "Citicoline Improves Verbal Memory in Aging," *Arch. Neurol.*, 53(5): 441-448 (1996).

\* cited by examiner

AGENT FOR PREVENTING OR IMPROVING DECLINE IN BRAIN FUNCTION

CROSS-REFERENCE TO RELATED APPLICATIONS

This patent application is the U.S. national phase of International Patent Application No. PCT/JP2013/080053, filed Oct. 30, 2013, which claims the benefit of Japanese Patent Application No. 2012-238542, filed on Oct. 30, 2012, which are incorporated by reference in their entireties herein.

TECHNICAL FIELD

The present invention relates to an agent for preventing or improving decline in brain function, comprising citrulline or a salt thereof and citicoline or a salt thereof as active ingredients.

BACKGROUND ART

Brain is the most significant region of central nerve system for information transmission via nerves such as motion and perception, and plays an important role in human mental activity such as feelings, emotions, reasoning or the like. Higher brain dysfunctions caused by cerebral trauma, cerebrovascular disorders, cerebritis, hypoxia or the like include a wide range of defects in memory, attention, executive functioning, social behavior and the like, and their characteristics vary depending on the part of the brain damage. Further, it is also reported that decline in brain function can be caused by fatigue (Non-Patent Literature 1), leading to decline in abilities such as memory learning, attention concentration, judgment or the like.

It is known that ischemic cerebrovascular disease causes brain neuronal cell death, leading to decline in brain function. The cause includes neurovascular damage, endothelial dysfunction, diminished cerebral blood flow or the like (Non-Patent Literature 2), and it is understood that a reduction of normal nitric oxide (NO) production in vascular endothelial cells and diminished cerebral blood flow cause brain neuronal cell death and decline in brain function. In other words, it is expected that brain neuronal cells can be protected and decline in brain function can be prevented or improved by enhancing NO production in vascular endothelial cells and cerebral blood flow.

Citrulline is one of amino acids present as free form and is not used as a constituent for protein synthesis in vivo. In the body, citrulline serves as a precursor of arginine in arginine biosynthesis or an important component of NO cycle involved in NO supply. Ingested citrulline is mostly converted to arginine in the kidney and produced arginine is efficiently supplied systemically (Non-Patent Literature 3).

Arginine is an amino acid to be a direct substrate of nitric oxide (NO) synthase. Moreover, arginine is an intermediate in the urea cycle in the liver, and plays an important role in detoxication of ammonia produced in the body. NO synthesized from arginine as a substrate exerts a variety of physiological functions for maintaining normal vascular functions, including vasodilatation, inhibition of LDL oxidation, inhibition of platelet aggregation, anti-proliferation effect on smooth muscle cells, antioxidant effect and the like.

It is reported that ingestion of citrulline shows an anti-arteriosclerosis action and improves blood circulation via the production of the vasodilator NO (Non-Patent Literature 4), and citrulline is widely used around US as a food material for producing NO to improve blood circulation. Citrulline is also used in Europe as an anti-fatigue drug in the form of citrulline-malate.

Citicoline is a water-soluble substance that is biosynthesized from choline phosphate and cytidine triphosphate in animals, yeasts or the like. Citicoline is involved in the biosynthesis of phosphatidylcholine which is a component of cell membrane, acetylcholine which is a neurotransmitter, or the like. It is also reported that citicoline, once orally ingested, is degraded into choline and uridine during intestinal absorption, and citicoline is reconstituted in the brain (Non-Patent Literature 5).

It is reported that ingestion of citicoline improves prognosis of acute cerebral infarction (Non-Patent Literature 6), cognitive function in Alzheimer's-type dementia (Non-Patent Literature 7) or the like. Owing to these functions, citicoline has been used as a medicine for the improvement of brain metabolism, impaired consciousness and pancreatitis in Japan and as a food material for the improvement or amelioration of brain function in foreign countries.

Until now, there have been reports about improvement of attention concentration by oral ingestion of citrulline (Patent Literature 1) and improvement of memory learning ability by intraperitoneal injection of arginine (Non-Patent Literature 8). However, there have been no reports that a synergistic effect of preventing or improving decline in brain function can be obtained by using citrulline or a salt thereof in combination with citicoline or a salt thereof.

CITATION LIST

Patent Literature

[PTL1] WO 2009096505

Non Patent Literature

[NPL1] Journal of occupational health, 2007, Vol. 49, p. 203-208
[NPL2] Neuroscience, 1999, Vol. 91, p. 203-210
[NPL3] Amino Acids, 2005, Vol. 29, p. 177-205
[NPL4] PNAS, 2005, Vol. 102, p. 13681-13686
[NPL5] Journal of Neuroscience Research, 1999, Vol. 58-5, p. 697-705
[NPL6] Stroke, 2002, Vol. 33, p. 2850-2857
[NPL7] Methods and findings in experimental and clinical pharmacology, 1999, Vol. 21-9, p. 633-644
[NPL8] Psychopharmacology, 2003, Vol. 167, p. 291-296

SUMMARY OF INVENTION

Technical Problem

An objection of the present invention is to provide an agent for preventing or improving decline in brain function such as decreased perception ability, decreased memory learning ability, decreased thinking ability, decreased concentration, decreased attention, decreased judgment ability, depression, and decreased exercise performance caused thereby.

Solution to Problem

The present invention relates to the following (1) to (13):
(1) An agent for protecting brain neuronal cells, comprising citrulline or a salt thereof and citicoline or a salt thereof as active ingredients.

(2) An agent for preventing or improving decline in brain function, comprising citrulline or a salt thereof and citicoline or a salt thereof as active ingredients.

(3) The agent for preventing or improving decline in brain function described in (2), wherein the decline in brain function is one or more selected from the group consisting of decreased perception ability, decreased memory learning ability, decreased thinking ability, decreased concentration, decreased attention, decreased judgment ability, depression, and decreased exercise performance caused thereby.

(4) A method for preventing or improving decline in brain function, wherein citrulline or a salt thereof and citicoline or a salt thereof are orally ingested as active ingredients.

(5) A method for preventing or improving decline in brain function, wherein an oral preparation comprising citrulline or a salt thereof and citicoline or a salt thereof as active ingredients is ingested.

(6) A method for preventing or improving decline in brain function, wherein citrulline or a salt thereof and citicoline or a salt thereof are orally ingested as active ingredients, provided that the prevention or improvement method does not include any method of surgery, therapy or diagnosis of humans practiced by medical doctor.

(7) A method for preventing or improving decline in brain function, wherein an oral preparation comprising citrulline or a salt thereof and citicoline or a salt thereof as active ingredients is ingested, provided that the prevention or improvement method does not include any method of surgery, therapy or diagnosis of humans practiced by medical doctor.

(8) Citrulline or a salt thereof and citicoline or a salt thereof for use in protecting brain neuronal cells.

(9) Citrulline or a salt thereof and citicoline or a salt thereof for use in preventing or improving decline in brain function.

(10) The citrulline or a salt thereof and the citicoline or a salt thereof described in (9), wherein the decline in brain function is one or more selected from the group consisting of decreased perception ability, decreased memory learning ability, decreased thinking ability, decreased concentration, decreased attention, decreased judgment ability, depression, and decreased exercise performance caused thereby.

(11) Use of citrulline or a salt thereof and citicoline or a salt thereof for the manufacture of an agent for protecting brain neuronal cells.

(12) Use of citrulline or a salt thereof and citicoline or a salt thereof for the manufacture of an agent for preventing or improving decline in brain function.

(13) The use described in (12), wherein the decline in brain function is one or more selected from the group consisting of decreased perception ability, decreased memory learning ability, decreased thinking ability, decreased concentration, decreased attention, decreased judgment ability, depression, and decreased exercise performance caused thereby.

Advantageous Effects of Invention

According to the present invention, a safe and effective agent for protecting brain neuronal cells and a safe and effective agent for preventing or improving decline in brain function, comprising citrulline or a salt thereof and citicoline or a salt thereof as active ingredients can be provided. According to the agent of the present invention, memory behavior can be synergistically and effectively improved by using citrulline or a salt thereof in combination with citicoline or a salt thereof, and excellent effect as the agent for preventing or improving decline in brain function can be obtained.

DESCRIPTION OF EMBODIMENTS

Citrulline used in the present invention includes L-citrulline and D-citrulline. Preferred is L-citrulline. Citrulline can be obtained by chemical synthesis, fermentation or the like. Citrulline can be also obtained by purchasing a commercially available product. A chemical synthesis method of citrulline includes the methods described in J. Biol. Chem., 122, 477(1938) and J. Org. Chem., 6, 410(1941).

A method for producing L-citrulline by fermentation includes the methods described in Japanese Patent Publication Nos. 1978-075387 and 1988-068091. In addition, L-citrulline and D-citrulline can also be purchased from Sigma-Aldrich Co., or the like.

The salts of citrulline include acid addition salts, metal salts, ammonium salts, organic amine addition salts, amino acid addition salts and the like. The acid addition salt includes inorganic acid salts such as hydrochloride, sulfate, nitrate, phosphate and the like, and organic acid salts such as acetate, maleate, fumarate, citrate, malate, lactate, α-ketoglutarate, gluconate, caprylate and the like. The metal salt includes alkali metal salts such as sodium salts, potassium salts and the like, alkaline earth metal salts such as magnesium salts, calcium salts and the like, aluminum salts, zinc salts and the like. The ammonium salt includes ammonium salts, tetramethylammonium salts and the like. The organic amine addition salt includes morpholine salts, piperidine salts and the like. The amino acid addition salt includes salts of glycine, phenylalanine, lysine, aspartic acid, glutamic acid and the like. Among the above-mentioned salts of citrulline, malate is preferably used. Other salts or two or more salts may be used in an appropriate combination.

Citicoline (citidine-5'-diphosphocholine (CDP-choline)) used in the present invention may be those obtained by any production method. The production method for citicoline includes the chemical synthesis (Japanese Patent Publication Nos. 1964-6541, 1967-1384, 1988-6558, and the like), the enzymatic method using a microorganism such as yeast or the like (Japanese Patent Publication Nos. 1973-2358, 1973-40757, 1973-40758, 1978-109996, 1979-14593, 1988-

313594, etc.) or the like. Citicoline can be also purchased from Sigma-Aldrich Co., or the like.

The citicoline comprised in the agent for preventing or improving decline in brain function of the present invention may exist as a salt thereof in the agent. The salt of citicoline includes the same salt as that of citrulline as mentioned above.

In the present invention, a compound involved in the synthesis of citicoline in vivo, for example, choline, uridine, or the like can be also used instead of citicoline.

A composition ratio of citrulline or a salt thereof to citicoline or a salt thereof in the agent for preventing or improving decline in brain function of the present invention is 1:100 to 100:1, preferably 1:50 to 50:1, particularly preferably 10:1 to 1:10 by weight.

As the agent for preventing or improving decline in brain function of the present invention, citrulline or a salt thereof and citicoline or a salt thereof can be administered as such, but it is usually preferred to provide the agent as various kinds of preparations.

The preparations comprise, as active ingredients, citrulline or a salt thereof and citicoline or a salt thereof and further may include any active ingredients. The preparations are produced according to any methods well known in the technical field of pharmaceutics by mixing the active ingredients with one or more kinds of pharmaceutically acceptable carriers.

Administration routes of the preparation may include oral administration and parenteral administration such as intravenous administration, intraperitoneal administration, subcutaneous administration or the like. Preferred is oral administration.

The preparation may be administered either in the form of oral preparations such as tablets, powders, granules, pills, suspensions, emulsions, infusionsdecoctions, capsules, syrups, liquids, elixirs, extracts, tinctures, fluid extracts and the like, or parenteral preparations such as injections, drops, creams, suppositories and the like. Preferred are oral preparations.

Liquid preparations suitable for oral administration such as syrups can be prepared by adding water, sugars such as sucrose, sorbitol, fructose or the like, glycols such as polyethylene glycol, propylene glycol or the like, oils such as sesame oil, olive oil, soybean oil or the like, antiseptics such as p-hydroxybenzoate ester or the like, paraoxybenzoic acid derivatives such as methyl paraoxybenzoate, preservatives such as sodium benzoate or the like, flavors such as strawberry flavor, peppermint or the like, or the like.

For example, tablets, powders, granules, or the like suitable for oral administration can be prepared by adding excipients such as sugars such as lactose, white sugar, glucose, sucrose, mannitol, sorbitol or the like, starch such as potato, wheat, corn or the like, inorganic substances such as calcium carbonate, calcium sulfate, sodium hydrogen carbonate, sodium chloride or the like, plant powders such as crystalline cellulose, licorice powder, powdered gentian or the like, disintegrating agents such as starch, agar, gelatin powder, crystalline cellulose, carmellose sodium, carmellose calcium, calcium carbonate, sodium hydrogen carbonate, sodium alginate or the like, lubricants such as magnesium stearate, talc, hydrogenated vegetable oil, macrogol, silicone oil or the like, binders such as polyvinyl alcohol, hydroxypropyl cellulose, methyl cellulose, ethyl cellulose, carmellose, gelatin, starch paste or the like, surfactants such as fatty acid esters or the like, plasticizers such as glycerin or the like.

The preparations suitable for oral ingestion or administration includes additives generally used in foods such as sweeteners, coloring agents, preservatives, thickening stabilizers, antioxidants, color developers, bleaching agents, fungicides, gum bases, bitter agents, enzymes, glazing agents, sour agents, seasonings, emulsifiers, enhancers, manufacture facilitating agents, flavors, spice extracts and the like.

The product forms or preparations suitable for oral ingestion or administration may be processed to, for example, tablets, powders, granules, pills, suspensions, emulsions, infusionsdecoctions, capsules, drinks, liquids, elixirs, extracts, tinctures, or fluid extracts in a unit packaging form per ingestion, depending on ingestion period, ingestion frequency, ingestion dose and the like. For example, "unit packaging form per ingestion" means that a pre-determined amount is packaged for each ingestion, and "unit packaging form for 1 week to 3 months" means that an ingestion dose for 1 week to 3 months is packaged. Examples of the unit packaging form include a form for prescribing a predetermined amount, such as a pack, a package, a bottle and the like.

With respect to the "unit packaging form per ingestion", for example, if the product form or preparation is a drink, 50 mg or more of citrulline or a salt thereof and citicoline or a salt thereof suspended or dissolved in a drink may be all packaged in a bottle for one ingestion.

With respect to the "unit packaging form for 1 week to 3 months", for example, it is ingested once a day to give a daily ingestion dose of 300 mg, 50 mg of citrulline or a salt thereof and citicoline or a salt thereof are contained in a tablet, and 42 to 540 tablets are packaged in each packaging form.

With respect to preparations suitable for parenteral administration, for example, injections preferably comprise a sterilized aqueous preparation containing citrulline or a salt thereof and citicoline or a salt thereof, which is isotonic to the recipient's blood. In the case of an injection, for example, a solution for injection is prepared using a carrier containing a salt solution, a glucose solution, or a mixture of a salt solution and a glucose solution.

One or more of auxiliary components selected from the above-described antiseptics, preservatives, excipients, disintegrating agents, lubricants, binders, surfactants, plasticizers and the like for oral preparations can also be employed in these parenteral preparations.

The concentrations of citrulline or a salt thereof and citicoline or a salt thereof in the agent for preventing or improving decline in brain function of the present invention are appropriately determined according to the kind of the preparation, the effect expected by the administration of the preparation or the like. Citrulline or a salt thereof is usually contained in an amount of 0.1 to 90% by weight, preferably 0.5 to 70% by weight, particularly preferably 1 to 50% by weight. Citicoline or a salt thereof is usually contained in an amount of 0.1 to 90% by weight, preferably 0.5 to 70% by weight, particularly preferably 1 to 50% by weight.

The administration dose and administration frequency of the agent for preventing or improving decline in brain function of the present invention vary depending on the administration form, the patient's age and body weight, and the characteristics or severity of the symptoms to be treated. Usually, the agent is administered once to several times per day in an amount to give a daily dose of 50 mg to 30 g, preferably 100 mg to 10 g, particularly preferably 200 mg to 3 g per adult in terms of citrulline or a salt thereof. Further, usually, the agent is administered once to several times per day in an amount to give a daily dose of 50 mg to 30 g, preferably 100 mg to 10 g, particularly preferably 200 mg to 3 g per adult in terms of citicoline or a salt thereof.

Ingestion or administration period is not particularly limited, but it is generally 1 day to 1 year, preferably 1 week to 3 months.

The agent for preventing or improving decline in brain function of the present invention can be used for protecting brain neuronal cells. The agent for preventing or improving decline in brain function of the present invention can be used for preventing or improving decline in brain function that is developed from brain neuronal cell death. Examples of the effects expected by preventing or improving decline in brain function includes prevention or improvement of decreased perception ability, decreased memory learning ability, decreased thinking ability, decreased concentration, decreased attention, decreased judgment ability, depression, decreased cognitive function and decreased exercise performance caused thereby.

Therefore, the agent for preventing or improving decline in brain function of the present invention is administered to a subject in need of preventing occurrence of these symptoms or a subject having these symptoms, thereby preventing or improving the symptoms.

Further, in the present invention, citrulline or a salt thereof and citicoline or a salt thereof may be used in order to manufacture the agent for preventing or improving decline in brain function.

Further, the present invention includes a method for protecting brain neuronal cells. The method of the present invention comprises the step of ingesting or administering citrulline or a salt thereof and citicoline or a salt thereof to a subject in need of protecting the brain neuronal cells in amounts sufficient to protect the brain neuronal cells of the subject.

Further, the present invention includes a method for preventing or improving decline in brain function. The method of the present invention includes the step of ingesting or administering citrulline or a salt thereof and citicoline or a salt thereof to a subject in need of preventing or improving decline in brain function, in amounts sufficient to prevent or improve decline in brain function of the subject.

Hereinafter, Experimental Examples regarding citrulline and citicoline for preventing or improving decline in brain function will be described.

EXPERIMENTAL EXAMPLE 10-week-old male C57BL/6J mice (CLEA Japan, Inc. approximately 25 g of average body weight per mouse) were preliminarily acclimated for 1 week, and provided for experiments. L-citrulline and citicoline were obtained from KYOWA HAKKO BIO CO., LTD.

C57BL/6J mice were divided into a sham-operation group (Group 1) and a bilateral common carotid arteries occlusion group, which was performed under halothane anesthesia for 20 minutes. One day after reperfusion, the bilateral common carotid arteries occlusion group was further divided into a distilled water-treated group (Group 2), a low-dose L-citrulline-treated group (40 mg/kg: Group 3), a low-dose citicoline-treated group (40 mg/kg: Group 4), a high-dose L-citrulline-treated group (100 mg/kg: Group 5), a high-dose citicoline-treated group (100 mg/kg: Group 6), and a combination treatment group of a low dose of L-citrulline and a low dose of citicoline (each 40 mg/kg: Group 7). Each sample was orally administered for 12 days. One week after starting administration, learning memory-improving effects were examined by a Y-maze test, a passive avoidance test, and a novel object recognition test. After evaluating learning memory functions, the hippocampus was removed and viability of hippocampal nerve cells was evaluated.

Y-Maze Test

In the Y-maze test, a Y-maze apparatus with three arms (50×16×32 cm) was used. Mice were placed at any one arm of the Y-maze and were allowed to explore freely through the maze for 8 minutes. The sequence of arm entries was recorded. The number of entries into each arm was counted during the measurement time, which was defined as the total number of entries. Of them, the successive entry into the three different arms was examined, and this number was defined as the spontaneous alternation behavior number. The spontaneous alternation behavior number was divided by (the total number of arm entries minus two), and then multiplied by 100, which was defined as the spontaneous alternation behavior rate (Alternation) and used as an index for spontaneous alternation behavior.

Figure 1:
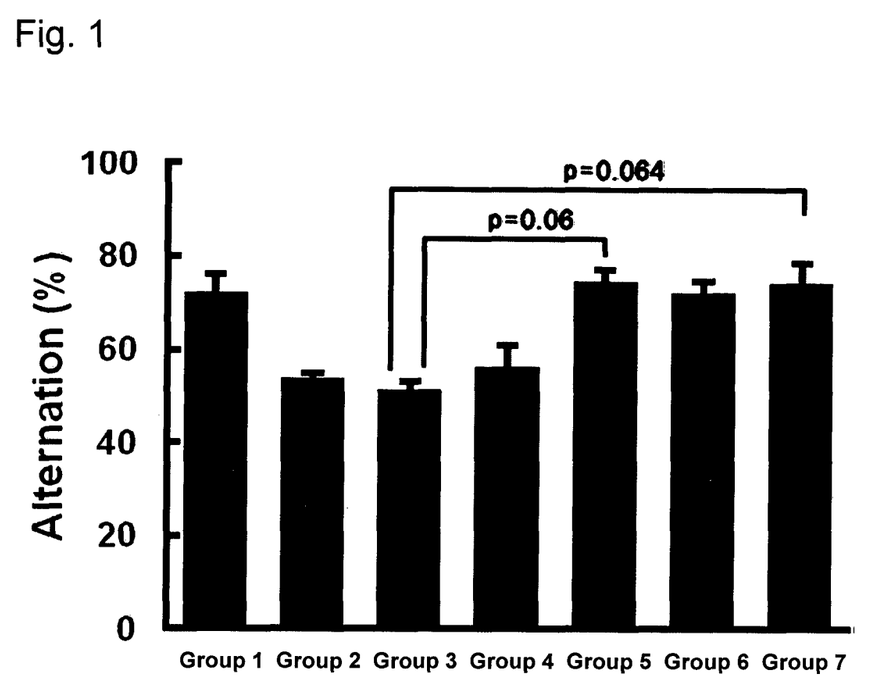
FIG. 1 shows spontaneous alternation behavior rate (Alternation) in the Y-maze test after administration of each concentration of the sample to mice for 7 days. Mean±standard error. N=4 to 6. There are significant differences between different letters.

As shown in FIG. 1, a low Alternation was observed in Group 2, compared to Group 1. Compared to Group 2, a high Alternation was observed in Group 7 that is a combination group of Group 3 and Group 4, in each of which Alternation cannot be improved. An improved effect of memory behavior was recognized in Group 7, equivalent to those of Group 5 and Group 6.

Passive Avoidance Test

The passive avoidance test was performed using a box consisting of dark (25×25×25 cm) and light compartments (14×10×25 cm) and being equipped with an electrical stimulation apparatus at the bottom of the dark compartment. During training, as soon as the mouse entered the dark compartment from the light compartment, the door was closed, and an electrical stimulation (0.3 mA, for 2 seconds) was delivered. Twenty four hours after training, the mouse was placed again in the light compartment, and the latency time spent in the light compartment was recorded with a maximum latency of 300 seconds.

Figure 2:
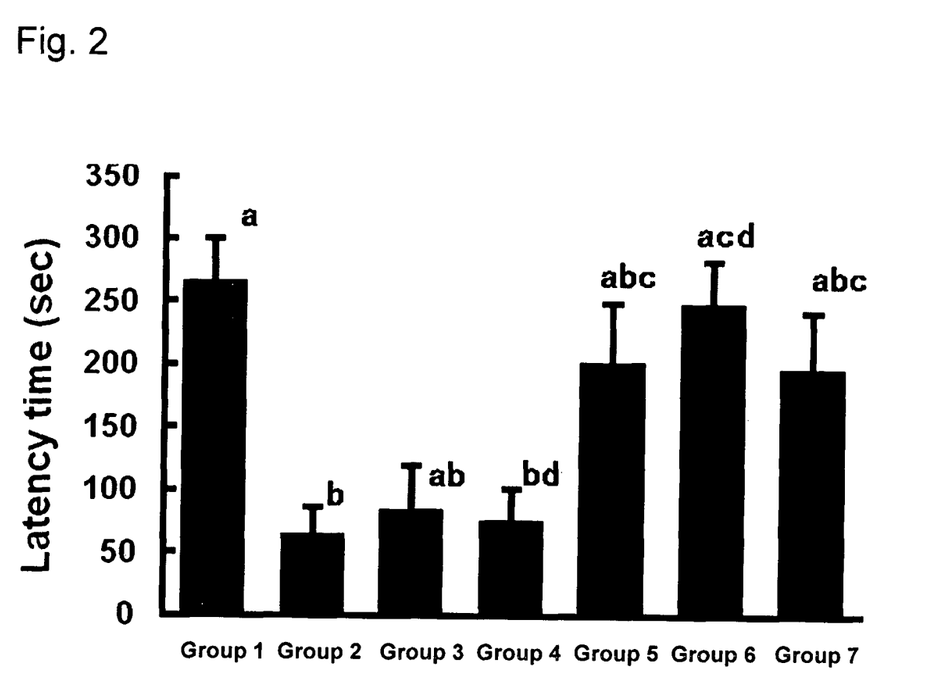
FIG. 2 shows the time spent in the light compartment (Latency time) in the passive avoidance test after administration of each concentration of the sample to mice for 7 days. Mean±standard error. N=4 to 6. There are significant differences ($p<0.05$) between different letters.

As shown in FIG. 2, a significantly low latency time was observed in Group 2, compared to Group 1. Compared to Group 2, a high latency time was observed in Group 7 that is a combination group of Group 3 and Group 4, in each of which the latency time cannot be improved. An improved effect of memory behavior was recognized in Group 7, equivalent to those of Group 5 and Group 6.

Novel Object Recognition Test

The novel object recognition test was performed after mice were individually acclimated to the open field apparatus (35×25×35 cm) for 2 days. During training, mice were allowed to explore freely for 10 minutes in an apparatus where two identical objects were symmetrically placed. After 1 hour, one object was replaced by a novel object, and mice were allowed to explore freely for 5 minutes. Object exploration was defined as standing on the objects, touching the object with the nose, or sniffing the object within 1 cm from the object. A ratio of the frequency of exploring the familiar or novel object over the total exploration frequency was calculated, and used as an index for visual recognition memory.

Figure 3:
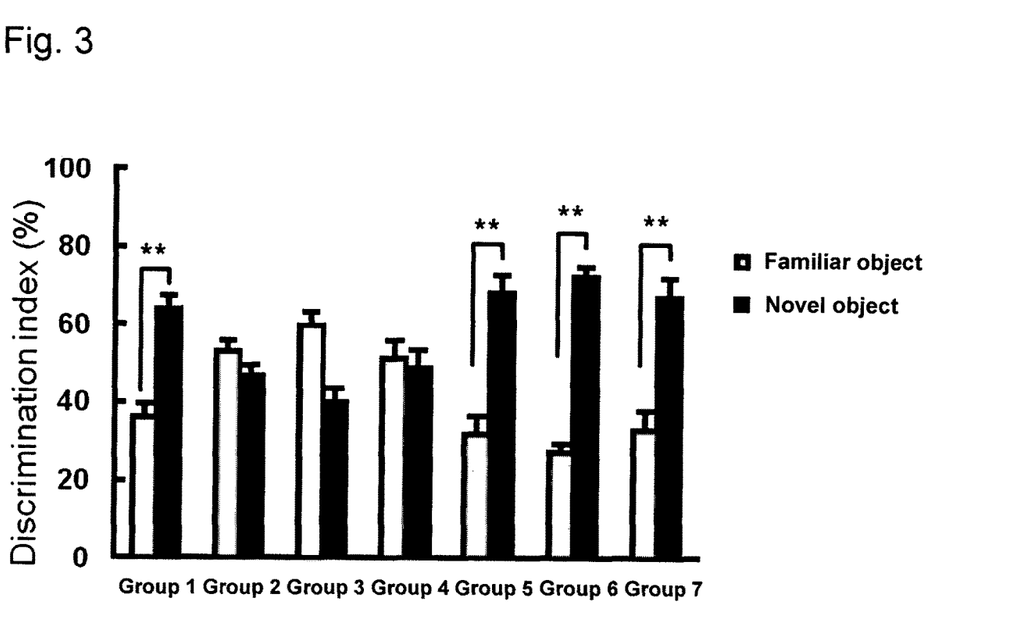
FIG. 3 shows a ratio of the frequency of exploring the familiar and novel objects in the novel object recognition test after administration of each concentration of the sample to mice for 7 days. Mean±standard error. N=4 to 6. ** indicates significant differences ($p<0.01$) between the familiar and novel objects.

As shown in FIG. 3, the increase in the frequency of exploring the novel object observed in Group 1 was not observed in Group 2. A significant increase in the frequency of exploring the novel object was observed in Group 7 that is a combination group of Group 3 and Group 4, in each of which the frequency of exploring the novel object cannot be increased. A remarkably improved effect of memory behavior was recognized in Group 7, equivalent to those of Group 5 and Group 6.

Evaluation of Viability of Hippocampal Nerve Cells

Twelve days after bilateral occlusion of the common carotid arteries, mice were anesthetized with pentobarbital sodium, and perfused with ice-cold phosphate buffer (PBS, pH 7.4) until the blood in the body was completely removed. Immediately, mice were perfused with a fixative solution containing 4% paraformaldehyde. The brain tissues were fixed at 4° C. for 24 hours, and coronal sections having a thickness of 50 μm were prepared. Serial sections containing the hippocampus were stained with propidium iodide (PI, 5 μmol/L) dissolved in PBS and observed under a fluorescent microscope. Surviving and non-surviving nerve cells in the CA1 pyramidal cell layer of the hippocampus were counted at 1.4 to 1.8 mm posterior to bregma, and cells with PI-positive nuclei and typical morphological characteristics were defined as surviving nerve cells. The cell viability was calculated from a ratio to the average number of surviving nerve cells in Group 1.

Figure 4:
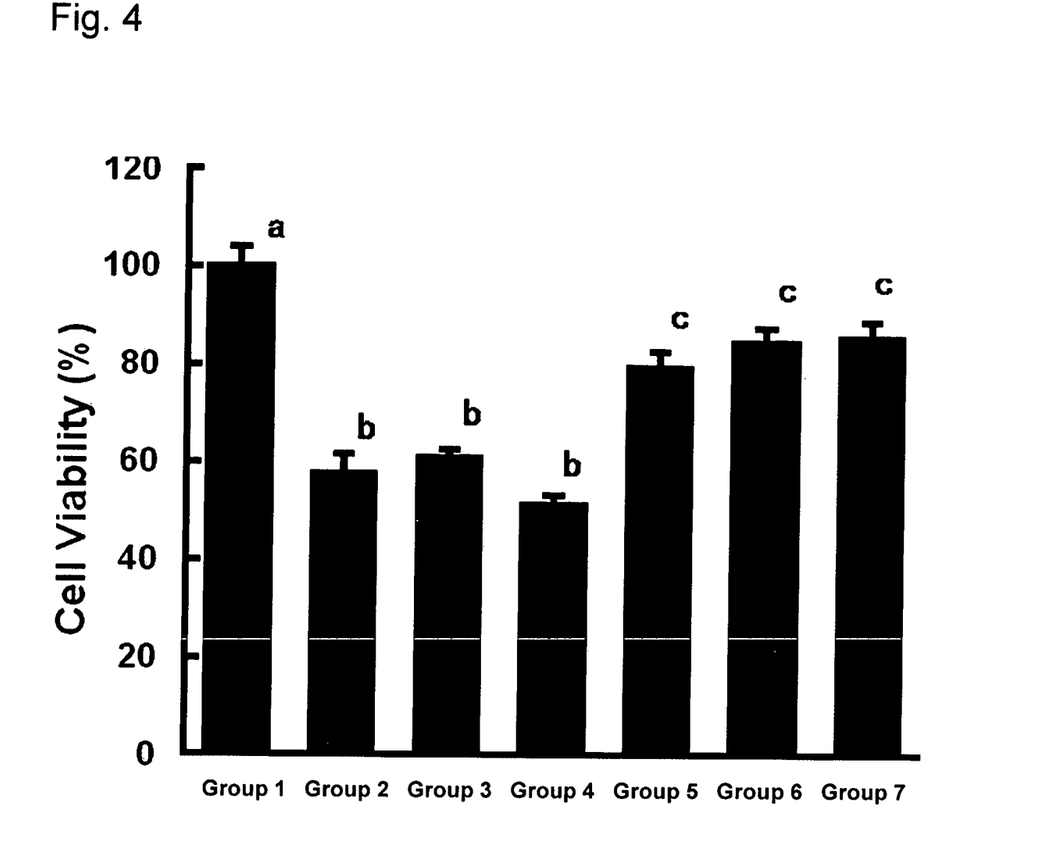
FIG. 4 shows the viability of hippocampal nerve cells after administration of each concentration of the sample to mice for 12 days. Mean±standard error. N=8. There are significant differences ($p<0.05$) between different letters.

As shown in FIG. 4, a significant reduction in the viability of hippocampal neurons was observed in Group 2, compared to Group 1. Compared to Group 2, a significantly high viability of hippocampal nerve cells was observed in Group 7 that is a combination group of Group 3 and Group 4, in each of which the viability of hippocampal nerve cells cannot be improved. A nerve cell-protecting effect was recognized in Group 7, equivalent to those of Group 5 and Group 6.

Taken together, it was clarified that the memory behavior can be synergistically and effectively improved by using citrulline in combination with citicoline, suggesting that the agent of the present invention is excellent in the prevention or improvement of decline in brain function.

Hereinafter, Examples of the present invention will be described.

Example 1

Preparation of Tablet Containing Citrulline and Citicoline 120 kg of L-citrulline, 120 kg of citicoline, 19 kg of cyclic oligosaccharide, 57 kg of cellulose, and 1 kg of pullulan were granulated using a fluid bed granulator dryer. The granulated product thus obtained and 3 kg of calcium stearate were mixed using a conical blender, and compression-molded in a rotary compression molding machine to give a tablet.

Example 2

Preparation of Enteric Tablet Containing Citrulline and Citicoline

The surface of the tablet prepared in Example 1 was coated with a shellac solution to give an enteric tablet.

Example 3

Preparation of Enteric Capsule Containing Citrulline and Citicoline 120 kg of L-citrulline, 120 kg of citicoline, 19 kg of cyclic oligosaccharide, 57 kg of cellulose, 3 kg of calcium stearate and 1 kg of pullulan were mixed using a conical blender. 20 kg of the obtained mixture and 0.2 kg of silicon dioxide were mixed and stirred. The obtained mixture was fed into a capsule filling machine, and filled in hard capsules to give a hard capsule. The surface of the obtained hard capsule was coated with a zein solution to give an enteric capsule.

Example 4

Preparation of Drink Containing Citrulline and Citicoline (1)

1.28 kg of L-citrulline, 1.28 kg of citicoline, 3 kg of erythritol, 0.05 kg of citric acid, 3 g of artificial sweetener, and 0.06 kg of flavor were dissolved in 50 L of water at 70° C. under stirring, and the solution was adjusted to pH 3.3 with citric acid. The mixture was sterilized by plate sterilization and filled in a bottle. Then, the bottle is sterilized by pasteurizer to give a drink.

Example 5

Preparation of Drink Containing Citrulline and Citicoline (2)

20 mg of L-citrulline, 20 mg of citicoline, 20 mg of L-arginine, a proper amount of fructose glucose syrup, salt, citric acid, flavor, Na citrate, Ca lactate, ferric pyrophosphate, Ca gluconate, K chloride, Mg chloride, and a sweetener were blended to give a 555 mL of drink.

Example 6

Preparation of Drink Containing Citrulline and Citicoline (3)

100 mg of L-citrulline, 100 mg of citicoline, 100 mg of L-arginine, 2.5 mg of L-alanine, 2.5 mg of L-glycine, 2.5 mg of L-leucine, 1.3 mg of L-isoleucine, 1.3 mg of L-valine and a proper amount of a flavor and a sweetener were blended to give a 300 ml of drink.

The present application is based on Japanese patent Application No. 2012-238542 filed on Oct. 30, 2012, the entire contents of which are incorporated hereinto by reference. All references cited herein are incorporated in their entirety.

INDUSTRIAL APPLICABILITY

According to the present invention, an agent for preventing or improving decline in brain function such as decreased perception ability, decreased memory learning ability, decreased thinking ability, decreased concentration, decreased attention, decreased judgment ability, depression, and decreased exercise performance caused thereby, comprising citrulline or a salt thereof and citicoline or a salt thereof as active ingredients is provided. According to the agent of the present invention, memory behavior can be synergistically and effectively improved by using citrulline or a salt thereof in combination with citicoline or a salt thereof, and excellent effect as the agent for preventing or improving decline in brain function can be obtained.

The invention claimed is:

1. A method for improving memory behavior, improving visual recognition memory, and/or protecting hippocampal nerve cells in a human subject comprising orally ingesting an effective amount of the combination of (a) citrulline or a salt thereof and (b) citicoline or a salt thereof, thereby improving memory behavior, improving visual recognition memory, and/or protecting hippocampal nerve cells in the subject, wherein the subject has experienced a cerebral trauma, cerebrovascular disorder, cerebritis, hypoxia, or carotid artery occlusion, wherein citrulline or a salt thereof and citicoline or a salt thereof are each orally ingested at a dose of 200 mg/day, and wherein the improvement in memory behavior or visual recognition is in comparison to the memory behavior or visual recognition of the subject immediately prior to the first dose of citrulline and citicoline.

2. The method of claim 1, wherein an oral preparation comprising citrulline or a salt thereof and citicoline or a salt thereof is ingested by the subject.

3. The method of claim 1, wherein the method does not include surgery, therapy, or diagnosis of a subject by a medical doctor.

4. The method of claim 2, wherein the method does not include surgery, therapy, or diagnosis of the subject by a medical doctor.

5. The method of claim 1, wherein the subject suffers from depression or has one or more impairments in perception ability, memory learning ability, thinking ability, concentration, attention, judgment ability, and exercise performance caused by a decline in brain function.

6. The method of claim 2, wherein the subject suffers from depression or has one or more impairments in perception ability, memory learning ability, thinking ability, concentration, attention, judgment ability, and exercise performance caused by a decline in brain function.

7. The method of claim 2, wherein memory behavior is improved in the subject.

8. The method of claim 2, wherein visual recognition memory is improved in the subject.

9. The method of claim 2, wherein hippocampal nerve cells are protected in the subject.

10. The method of claim 1, wherein memory behavior is improved in the subject.

11. The method of claim 1, wherein visual recognition memory is improved in the subject.

12. The method of claim 1, wherein hippocampal nerve cells are protected in the subject.

13. A method of protecting brain neuronal cells comprising orally administering an effective amount of the combination of (a) citrulline or a salt thereof and (b) citicoline or a salt thereof to a human subject in need thereof, wherein the subject has experienced a cerebral trauma, cerebrovascular disorder, cerebritis, hypoxia, or carotid artery occlusion, thereby protecting brain neuronal cells in the subject, wherein citrulline or a salt thereof and citicoline or a salt thereof are each orally administered at a dose of 200 mg/day.

14. The method of claim 13, wherein an oral preparation comprising citrulline or a salt thereof and citicoline or a salt thereof is administered to the subject.

* * * * *